United States Patent
Berthon-Jones et al.

(10) Patent No.: US 6,588,422 B1
(45) Date of Patent: Jul. 8, 2003

(54) METHOD AND APPARATUS TO COUNTERBALANCE INTRINSIC POSITIVE END EXPIRATORY PRESSURE

(75) Inventors: Michael Berthon-Jones, Leonay (AU); Michael David Hallett, Balgowlah Heights (AU)

(73) Assignee: ResMed Ltd., North Ryde (AU)

( * ) Notice: Subject to any disclaimer, the term of this patent is extended or adjusted under 35 U.S.C. 154(b) by 0 days.

(21) Appl. No.: 09/482,251

(22) Filed: Jan. 13, 2000

Related U.S. Application Data

(60) Provisional application No. 60/116,121, filed on Jan. 15, 1999.

(51) Int. Cl.$^7$ .......................... A61M 16/00; A62B 7/00; F16K 31/02
(52) U.S. Cl. .......................... 128/204.23; 128/204.18; 128/204.21
(58) Field of Search ................. 128/204.18, 204.21, 128/204.23, 204.26

(56) References Cited

U.S. PATENT DOCUMENTS

| | | | | |
|---|---|---|---|---|
| 5,107,830 A | * | 4/1992 | Younes ................. | 128/204.18 |
| 5,117,819 A | * | 6/1992 | Servidio et al. ........ | 128/204.18 |
| 5,148,802 A | * | 9/1992 | Sanders et al. ......... | 128/204.18 |
| 5,174,287 A | * | 12/1992 | Kallok et al. .......... | 128/200.24 |
| 5,239,995 A | * | 8/1993 | Estes et al. ............ | 128/204.23 |
| 5,345,930 A | * | 9/1994 | Cardinal et al. ....... | 128/205.24 |
| 5,458,137 A | | 10/1995 | Axe et al. | |
| 5,490,502 A | * | 2/1996 | Rapoport et al. ....... | 128/204.23 |
| 5,492,113 A | * | 2/1996 | Estes et al. ............ | 128/204.23 |
| 5,535,738 A | * | 7/1996 | Estes et al. ............ | 128/204.23 |
| 5,549,106 A | * | 8/1996 | Gruenke et al. ....... | 128/204.23 |
| 5,551,419 A | * | 9/1996 | Froehlich et al. ...... | 128/204.23 |
| 5,598,838 A | * | 2/1997 | Servidio et al. ........ | 128/204.23 |
| 5,617,846 A | | 4/1997 | Graetz et al. | |
| 5,704,345 A | * | 1/1998 | Berthon-Jones ........ | 128/204.23 |
| 5,803,066 A | * | 9/1998 | Rapoport et al. ....... | 128/204.23 |
| 5,845,636 A | * | 12/1998 | Gruenke et al. ....... | 128/204.23 |
| 5,865,173 A | * | 2/1999 | Froehlich .............. | 128/204.23 |
| 6,029,665 A | * | 2/2000 | Berthon-Jones ........ | 128/204.23 |

FOREIGN PATENT DOCUMENTS

| | | |
|---|---|---|
| CA | 1108505 A | 9/1981 |
| EP | 776672 A1 | 6/1997 |

OTHER PUBLICATIONS

Servocontrolled Generator to Measure Respiratory Impedance from 0.25 to 26 Hz in Ventilated Patients at Different PEEP Levels; European Respiratory Journal 1995; 8; Technical Note, pp 1222–27; by R. Farré, M. Ferrer, M. Rotger, and D. Navajas.

Respiratory Mechanics Studied by Forced Oscillations During Artificial Ventilation; European Respiratory Journal 1993; 6; pp 772–84; by R. Peslin, J. Felicio Da Silva, C. Duvivier, and F. Chabot.

The Role of PEEP in Patients with Chronic Obstructive Pulmonary Disease During Assisted Ventilation; European Respiratory Journal 1990; 3; pp 818–22; by A. Rossi, R. Brandolese, J. Milic–Emili, S.B. Gottfried.

* cited by examiner

*Primary Examiner*—Weilun Lo
*Assistant Examiner*—Joseph F. Weiss, Jr.
(74) *Attorney, Agent, or Firm*—Gottlieb, Rackman & Reisman, P.C.

(57) ABSTRACT

The invention prevents dynamic airway compression during ventilatory support of a patient. The respiratory airflow is determined by measurement or calculation, and a measure of the degree of dynamic airway compression is derived from the determined airflow. This measure is servo-controlled to be zero by increasing expiratory pressure if the measure of the degree of dynamic airway compression is large or increasing, and by reducing expiratory pressure if the measure of the degree of dynamic airway compression is small or zero.

24 Claims, 1 Drawing Sheet

Figure 1:
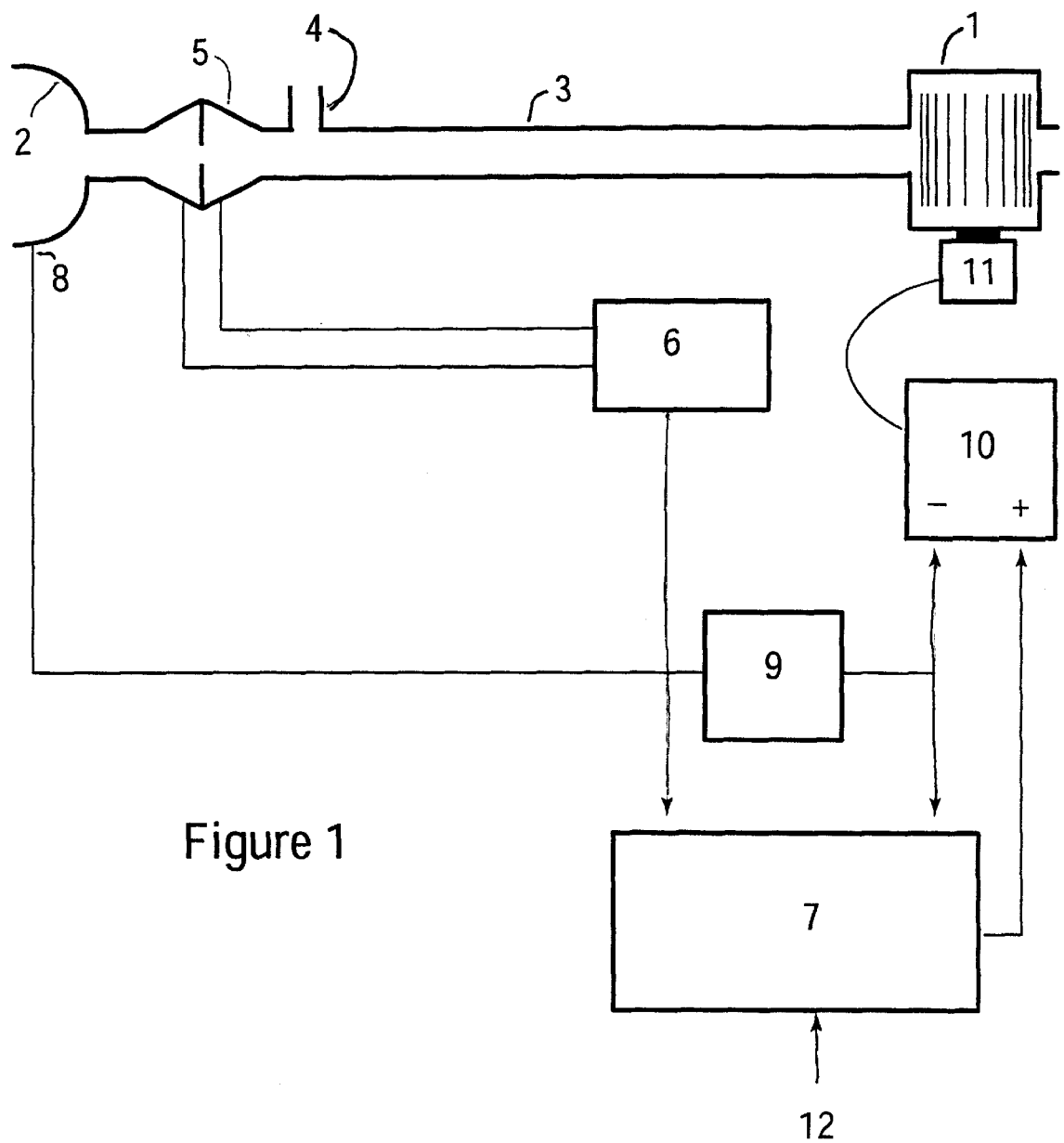

METHOD AND APPARATUS TO COUNTERBALANCE INTRINSIC POSITIVE END EXPIRATORY PRESSURE

This application claims the benefit of U.S. provisional application No. 60/116,121, filed Jan. 15, 1999.

FIELD OF THE INVENTION

This invention pertains to the field of ventilatory support for respiratory failure, particularly due to lung disease, and in particular to automatically providing sufficient end expiratory pressure to unload intrinsic positive end expiratory pressure (PEEPi)

BACKGROUND OF THE INVENTION

Subjects with chronic airflow limitation (CAL) due, for example, to emphysema and chronic bronchitis, may require ventilatory assistance, particularly during periods of acute exacerbation, or routinely at night.

Ventilatory support can reduce the work of breathing, reduce the sensation of breathlessness, and improve blood gases (oxygen and carbon dioxide levels). In subjects with CAL, most of the work of breathing is due to the high airway resistance. Approximately two thirds of this resistance is relatively fixed, and due to narrowing of the airways. However, of the order of one third of the resistance is due to dynamic airway compression during expiration. Dynamic airway compression occurs when the pleural pressure exceeds the pressure in the lumen of the airway during expiration, causing flow to become independent of effort.

In a normal subject, the alveolar pressure decays exponentially during expiration, so that the expiratory flow and alveolar pressure (relative to atmospheric) are both approximately zero at the end of expiration, and the lungs and chest wall have returned to their passive equilibrium volume $V_R$. In patients with CAL, however, as a result of dynamic airway compression and fixed reduced expiratory flow rate, it is not possible for the lungs to return to $V_R$ in the time allowed before the start of the next inspiration. The chest is hyperinflated. The alveolar pressure remains positive, on the order of 5 to 15 $cmH_2O$ at the end of expiration. This raised alveolar pressure is termed intrinsic positive end expiratory pressure, or PEEPi. (Other names for the phenomenon are covert PEEP and occult PEEP.)

An important effect of the hyperinflation is that the patient must overcome the elastic recoil of the hyperinflated chest wall before inspiratory airflow can commence. The PEEPi is said to act as an inspiratory threshold load. A further undesirable effect of PEEPi is that during artificial mechanical ventilatory support, it interferes substantially with the triggering of the ventilator, causing patient-machine asynchrony.

It is now well understood that the addition of a counterbalancing external positive end expiratory pressure (called external PEEP, or just PEEP), approximately equal in magnitude to PEEPi, is of great benefit. First, it prevents dynamic airway compression, permitting greater expiratory airflow. Second, it balances the inspiratory threshold load. Third, it improves triggering of a ventilator by the patient.

Use of excessive PEEP, however, can be disadvantageous and even dangerous. Excessive PEEP above and beyond PEEPi will cause yet further hyperinflation. This will result in stiffening of the lung and chest wall, and an increase in the elastic work of breathing. It will also cause reduced cardiac output, and can lead to barotrauma. Further, the peak inspiratory airway pressure during ventilatory support cannot be arbitrarily increased without either exceeding the capacity of the ventilator, or reaching a pressure that is itself dangerous. Finally, excessive external PEEP will also reduce the possible airway pressure excursion or headroom available for lung inflation.

Therefore, it is advisable when applying external PEEP to set the external PEEP as close as possible to PEEPi. Since PEEPi varies from time to time, depending on a number of factors including, for example, the resistance of the small airways and the respiratory rate, both of which change with changing sleep stage, chest infection, or bronchospasm, it is desirable to be able to make multiple, or even continuous, measurements of PEEPi in order to optimize external PEEP.

A typical patient in an intensive care unit is heavily sedated and paralyzed during ventilatory support, and it is straightforward to measure the PEEPi. It is necessary only to occlude the airway during late expiration, and measure the airway pressure, which, after a few seconds of equilibration, will equal static PEEPi. Since the lung injury in CAL is usually markedly heterogeneous, different alveoli will have different end expiratory pressures, and static PEEPi is therefore a weighted average across all alveoli.

Another known method which is suitable for use in the paralyzed sedated patient is to measure the airway pressure at the start of machine inspiratory effort, and again at the start of actual inspiratory airflow. The difference between these two pressures is the dynamic PEEPi. Dynamic PEEPi reflects the end expiratory pressure in the least abnormal lung units, and substantially underestimates static PEEPi.

These simple methods do not work for patients who are not sedated and paralyzed, and who are making spontaneous breathing efforts, because they do not take into account the patients' own respiratory muscle efforts.

One known method that is used with such patients requires a Muller manoeuvre (maximal inspiratory effort) during catheterization of the oesophagus and stomach, and is therefore completely unsatisfactory for repeated or continuous measurements in the ambulatory patient or the patient who is being treated at home long-term.

Methods for measuring the airway conductance in spontaneously breathing patients using oscillometry are taught by Peslin et al., *Respiratory Mechanics Studied by Forced Oscillations During Mechanical Ventilation*, Eur Respir J 1993; 6:772–784, and by Farre et al., *Servo Controlled Generator to Measure Respiratory Impedance from0.25 to 26Hz in Ventilated Patients at Different PEEP Levels*, Eur Respir J 1995; 8:1222–1227. These references contemplate separate measurements for inspiration and expiration. Oscillometry requires modulation of the airway pressure at a high frequency, such as 4 Hz, and measurement of the resultant modulation of the respiratory airflow at that frequency. However, these references fail to describe servo-controlling of ventilation to increase or decrease PEEP so that the inspiratory arid expiratory conductances are approximately equal.

Oscillometry has been used to control nasal CPAP (see U.S. Pat. No. 5,617,846) or bilevel CPAP for the treatment of obstructive sleep apnea (see U.S. Pat. No. 5,458,137). The problem there is essentially opposite to the problem under consideration here. In obstructive sleep apnea, there is increased resistance during inspiration, and the above two patents teach that increased resistance during inspiration can be treated by an increase in pressure. In patients with CAL and dynamic airway compression, there is increased resistance during expiration.

There is no known method or apparatus which can automatically or continuously control a ventilator or CPAP apparatus in conscious spontaneously breathing patients in order to prevent expiratory airflow limitation or to unload PEEPi in CAL.

Yet another known method for estimating PEEPi, taught, for example, by Rossi et al., *The Role of PEEP in Patients with Chronic Obstructive Pulmonary Disease during Assisted Ventilation*, Eur Respir J 1990; 3:818–822, is to examine the shape of the expiratory flow-volume curve, which has been observed to be exponential, if there is no dynamic airway compression. The reference further notes that in the absence of PEEPi, the flow-volume curve becomes a straight line.

The above known art only contemplates the application of an external pressure which is constant during any one expiratory cycle. However, the elastic recoil of the lung is higher at high lung volume, and lower at low lung volume. Therefore, it may be advantageous to find the minimum external pressure at each moment in time during an expiration that will prevent dynamic airway compression during that expiration.

It is an object of our invention to vary the ventilatory pressure during expiration as a function of the degree of the patient's dynamic airway compression.

It is another object of our invention to vary the ventilatory pressure automatically based solely on continuous measurements that are already taken in conventional CPAP and ventilator apparatuses.

SUMMARY OF THE INVENTION

The present invention seeks to provide continuous and automatic adjustment of the expiratory pressure during ventilatory support, so as to substantially prevent dynamic airway compression and unload intrinsic PEEP with the smallest amount of external expiratory pressure.

The basic method of the invention prevents dynamic airway compression during ventilatory support using a conventional interface to a patient's airway such as a face mask, nose mask, or endotracheal or tracheotomy tube, and providing the interface with an exhaust and a supply of breathable gas at a variable pressure as is known in the CPAP and ventilatory arts. The respiratory airflow is determined by measurement or calculation, and a measure of the degree of dynamic airway compression is derived. This measure is servo-controlled, preferably to be zero, by increasing expiratory pressure if the measure of the degree of dynamic airway compression is large or increasing, and by reducing expiratory pressure if the measure of the degree of dynamic airway compression is small or zero.

The measure of the degree of dynamic airway compression may be an instantaneous or pointwise measure within any given breath, and the step of servo-controlling the measure to be zero may similarly be performed pointwise within a given breath, so that the expiratory pressure is similarly varied pointwise within a breath. As an alternative to thus basing the airway compression determination and the servo control on multiple airflow determinations made within each individual respiratory cycle, the derivation of the measure of the degree of dynamic airway compression and the servo-controlling of the airway compression may be performed across a plurality of respiratory cycles.

During expiration, the expiratory pressure increase may be linear as a function of expired volume as will be described below.

The measure of the degree of dynamic airway compression is preferably derived by measuring the airway conductance separately during the inspiratory and expiratory portions of one or more respiratory cycles, and calculating the measure of the degree of dynamic airway conductance as a function of the inspiratory conductance minus the expiratory conductance, or alternatively as the ratio of the inspiratory conductance to the expiratory conductance. The two separate conductances during inspiration and expiration may be measured by superimposing a high-frequency oscillation on the patient interface pressure, at a known or measured amplitude, identifying the inspiratory and expiratory portions of each respiratory cycle, measuring the component of the respiratory airflow at the high frequency separately over the inspiratory and expiratory portions of one or more respiratory cycles, and from these measurements and the determined pressure amplitude calculating the inspiratory airway conductance and the expiratory airway conductance.

Alternatively, the measure of the degree of dynamic compression may be derived from the shape of the expiratory airflow versus time curve. The measure is zero when the expiratory flow decays exponentially from the moment of the peak expiratory flow to end expiration, but is large when the expiratory flow decreases suddenly from the peak expiratory flow and is then steady but non-zero for the remainder of expiration. The measure may be the ratio of the mean expiratory flow during approximately the last 25% of expiratory time to the peak expiratory flow.

Further objects, features and advantages of the invention will become apparent upon consideration of the following detailed description in conjunction with the drawing which depicts illustrative apparatus for implementing the method of our invention.

DETAILED DESCRIPTION OF THE INVENTION

In the drawing, a blower 1 supplies breathable gas to a mask 2 in communication with a patient's airway via a delivery tube 3 and exhausted via an exhaust 4. Airflow at the mask 2 is measured using a pneumotachograph 5 and a differential pressure transducer 6. The mask flow signal from the transducer 6 is then sampled by a microprocessor 7. Mask pressure is measured at the port 8 using a pressure transducer 9. The pressure signal from the transducer 6 is then sampled by the microprocessor 7. The microprocessor 7 sends an instantaneous mask pressure request (i.e., desired) signal to a servo 10, which compares the pressure request signal with the actual pressure signal from the transducer 9 to control a fan motor 11. Microprocessor settings can be adjusted via a serial port 12.

It is to be understood that the mask could equally be replaced with a tracheotomy tube, endotracheal tube, nasal pillows, or other means of making a sealed connection between the air delivery means and the subject's airway.

The invention involves the steps performed by the microprocessor to determine the desired mask pressure. The microprocessor accepts the mask airflow and pressure signals, and from these signals determines the instantaneous flow through any leak between the mask and patient, by any convenient method. For example, the conductance of the leak may be estimated as the instantaneous mask airflow, low-pass filtered with a time constant of 10 seconds, divided by the similarly low-pass filtered square root of the instantaneous mask pressure, and the instantaneous leakage flow may then be calculated as the conductance multiplied by the square root of the instantaneous mask pressure. Respiratory airflow is then calculated as the instantaneous mask airflow minus the instantaneous leakage flow.

In the simple case of no intrinsic PEEP, the instantaneous pressure at the mask may be simply set as follows, in order to provide ventilatory support to the patient:

$$P = P_{INSP} \quad flow > 0 \text{ (inspiration)}$$

$$P = P_{EXP} \quad flow <= 0 \text{ (expiration)}$$

where $P_{EXP}$ is less than or equal to $P_{INSP}$. Typically, $P_{EXP}$ might be zero, and $P_{INSP}$ might be of the order of 10 to 20 cmH$_2$O.

Two embodiments for deriving a measure of the degree of expiratory airflow limitation will now be considered. In the first embodiment, airway conductance during inspiration is compared with airway conductance during expiration, and a higher conductance during inspiration indicates expiratory airflow limitation. Airway conductance is calculated by superimposing on the instantaneous mask pressure a 4-Hz oscillation of amplitude 1 cmH$_2$O, and measuring the component of the respiratory airflow signal at 4 Hz. The conductance may be calculated once for each half cycle of the 4-Hz oscillation. In order to identify inspiratory and expiratory halves of the respiratory cycle, the respiratory airflow is low-pass filtered to minimize the imposed 4-Hz oscillation, for example, by averaging measured respiratory airflow over a moving window of length 0.25 seconds. If the 4-Hz low-pass filtered flow is above a threshold such as 0.1 L/sec, it is taken to be the inspiratory half-cycle. Otherwise, it is taken as being the expiratory half-cycle.

Conductance over one or more inspiratory half-cycles, and over one or more expiratory half cycles is now calculated, using standard averaging or filtering techniques. The conductance during inspiration minus the conductance during expiration yields a first measure $M_1$ of the degree of dynamic airway compression. Preferably, $M_1$ can be normalized by dividing by the mean conductance over the entire breath or breaths, and a threshold value, for example, 0.2, can be subtracted so that only differences in conductance of 20% or more are regarded as indicative of dynamic airway compression. Thus, $M_1$ =(average conductance during inspiration–average conductance during expiration)/(average conductance over entire breath)–0.2.

Finally, it is necessary to adjust the expiratory pressure to servo-control the difference in conductance to be zero. This can be done for, example, by increasing $P_{EXP}$ by $(0.1)(M_1)$ cmH$_2$O per second. Using this method, if there is dynamic airway compression, $P_{EXP}$ will slowly increase until $M_1$ reaches zero, at which point there will be no further dynamic airway compression. Changes in the pressure required to prevent dynamic compression with the passage of time can be tracked. In an elaboration of this first embodiment, $M_1$ can be calculated as a function of the time into expiration, and the pressure at different points into expiration servo-controlled separately within a breath.

In the second embodiment for deriving a measure of the degree of expiratory airflow limitation, the degree of expiratory flow limitation is calculated from the shape of the expiratory flow versus time curve. The expiratory portion of each breath is identified, for example, by taking expiration as the period where airflow is less than 0.1 L/sec. The mean expiratory airflow during the final 25% of expiratory duration is calculated, and divided by the peak expiratory airflow. For a subject without expiratory airflow limitation, this ratio will be close to zero, and less than a threshold such as 0.2, whereas for a subject with expiratory airflow limitation, it will be larger, for example, in the range 0.2 to 0.6, with higher values indicating more severe dynamic airway compression. Therefore, a second measure of the degree of expiratory airflow limitation is $M_2$ =(mean expiratory flow during last 25% of expiratory time)/(peak expiratory flow)–threshold, where the threshold is, for example, 0.2.

In the final step in this second embodiment, if $M_2$ is positive, the expiratory pressure $P_{EXP}$ is increased slightly, for example by $(0.1)(M_2)$ cmH$_2$O per breath. Conversely, if $M_2$ is negative, $P_{EXP}$ is decreased slightly, for example, by $(0.1)(M_2)$ cmH$_2$O per breath.

A third embodiment, which can be used as an enhancement of the servo-controlling step in either of the above two embodiments, takes account of the fact that here is no dynamic compression at the start of expiration, and no external pressure is required to prevent dynamic compression at the start of expiration, but that dynamic compression develops as the elastic recoil decreases. Since the elastic recoil pressure decreases approximately linearly on expired volume, the external pressure required to be applied will increase approximately linearly as a function of expired volume. Therefore, in this third embodiment, expiratory pressure is set as:

$$P_{EXP}(t) = K \, V(t)/V_T$$

where $P_{EXP}(t)$ is the pressure at time t in the expiratory portion of a respiratory cycle, V(t) is the expired volume at time t into the expiration, and $V_T$ is the tidal volume of the previous inspiration. Thus, $V(t)V_T$ increases from 0 to 1 during expiration. The constant K is adjusted in order to servo-control either $M_1$, or $M_2$ to be zero, and will approximate PEEPi.

Although the invention has been described with reference to particular embodiments, it is to be understood that these embodiments are merely illustrative of the application of the principles of the invention. Numerous modifications may be made therein and other arrangements may be devised without departing from the spirit and scope of the invention.

What we claim is:

1. A method for preventing dynamic airway compression during ventilatory support of a patient, comprising the steps of:

providing an interface to the patient's airway, providing said interface with a supply of breathable gas at a controllable pressure and with an exhaust, providing a device for measuring respiratory airflow;

providing a device for calculating respiratory airflow and deriving a measure of the degree of dynamic airway compression;

determining respiratory airflow by way of measurement and calculation, varying the pressure at the patient interface so as to provide ventilatory support to the patient, from at least the determined respiratory airflow, deriving a measure of the degree of dynamic airway compression, and servo-controlling the measure of the degree of dynamic airway compression by increasing expiratory pressure if said measure is large or increasing, and reducing expiratory pressure if said measure is small or zero, wherein said measure of the degree of dynamic airway compression is derived by analysis of the shape of the expiratory airflow versus time curve.

2. A method as in claim 1 in which said measure of the degree of dynamic airway compression and said servo-controlling of the degree of dynamic airway compression are both based upon multiple respiratory airflow determinations made within each individual respiratory cycle.

3. A method as in claim 1 which said measure of the degree of dynamic airway compression and said servo-controlling of the degree of dynamic airway compression are both based upon a respiratory airflow determination made across a plurality of respiratory cycles.

4. A method as in claim 1 in which, during expiration, expiratory pressure is increased approximately linearly as a function of expired volume.

5. The method as in claim 1 in which said measure is zero when the expiratory airflow decays exponentially from the moment of the peak expiratory airflow to end expiration, but is large when the expiratory airflow decreases suddenly from the peak expiratory flow and is then steady but non-zero for the remainder of expiration.

6. The method as in claim 5 in which said measure is the ratio of the mean expiratory airflow during approximately the last 25% of expiratory time to the peak expiratory flow.

7. A method for preventing dynamic airway compression during ventilatory support of a patent, comprising the steps of:
   providing a variable pressure device to supply pressure to the patient's airway so as to provide ventilatory support,
   providing an apparatus for determining respiratory airflow and deriving a measure of the degree of dynamic airway compression;
   determining the patent's respiratory airflow,
   deriving a measure of the degree of dynamic airway compression as a function of the determined respiratory airflow by measuring the patient's airway conductance separately during the inspiratory and expiratory portions of at least one respiratory cycle, and
   increasing or decreasing expiratory pressure in accordance with the derived measure of the degree of dynamic airway compression,
   wherein the measure of the degree of dynamic airway conductance is calculated as a function of the difference between the inspiratory conductance and the expiratory conductance.

8. A method as in claim 7 in which the expiratory pressure is increased or decreased by servo-controlling the measure of the degree of dynamic airway compression.

9. The method as in claim 8 in which expiratory pressure is increased if said measure of the degree of dynamic airway compression is large or increasing, and expiratory pressure is reduced if said measure of the degree of dynamic airway compression is small or zero.

10. A method as in claim 7 in which expiratory pressure is increased if said measure of the degree of dynamic airway compression is large or increasing, and expiratory pressure is reduced if said measure of the degree of dynamic airway compression is small or zero.

11. A method as in claim 7 in which said measure of the degree of dynamic airway compression is based upon a respiratory airflow determination made across a plurality of respiratory cycles.

12. A method as in claim 7 in which the separate conductances during inspiration and expiration are measured in accordance with the sub-steps of:
   superimposing a high-frequency oscillation on the variable pressure provided to the patient's airway,
   identifying the inspiratory and expiratory portions of each respiratory cycle,
   measuring the component of the respiratory airflow at said high frequency, separately over the inspiratory and expiratory portions of at least one respiratory cycle, and
   calculating the inspiratory and expiratory airway conductances from the high-frequency component airflow measurements.

13. An apparatus for determining a pressure response to ameliorate dynamic airway compression during ventilatory support comprising:
   an interface to a patient's airway and an exhaust,
   a means for supplying breathable gas at a controllable pressure to the interface,
   a means for deriving an airflow signal from said interface, and
   a controller means with programming instructions for:
      (a) controlling a variation of the pressure at the interface to provide ventilatory support to the patient;
      (b) controlling a determination of a measure of a degree of dynamic airway compression at least from calculated data representing the airflow signal; and
      (c) servo-controlling the measure of the degree of dynamic airway compression by increasing the controllable pressure during expiration if the measure of the degree of dynamic airway compression is large or increasing, and decreasing the controllable pressure during expiration if the measure of the degree of dynamic airway compression is small or zero,
   wherein said measure of the degree of dynamic airway compression is derived by analysis of the shape of the expiratory airflow versus time curve.

14. The apparatus of claim 13 in which said measure of the degree of dynamic airway compression and said servo-controlling of said degree of dynamic airway compression are both based upon multiple respiratory airflow determinations made within each individual respiratory cycle.

15. The apparatus of claim 13 in which said measure of the degree of dynamic airway compression and said servo-controlling of said degree of dynamic airway compression are both based upon a respiratory airflow determination made across a plurality of respiratory cycles.

16. The apparatus of claim 13 in which said instructions, during expiration, control an increase in expiratory pressure approximately linearly as a function of expired volume.

17. The apparatus of claim 13 in which said measure is zero when the expiratory airflow decays exponentially from the moment of the peak expiratory airflow to end expiration, but is large when the expiratory airflow decreases suddenly from the peak expiratory flow and is then steady but non-zero for the remainder of expiration.

18. The apparatus of claim 17 in which said measure is the ratio of the mean expiratory airflow during approximately the last 25% of expiratory time to the peak expiratory flow.

19. An apparatus for determining a pressure response to ameliorate dynamic airway compression during ventilation support comprising:
   an interface to a patient's airway and an exhaust,
   a means for supplying breathable gas at a controllable pressure to the interface,
   a transducer for determining an airflow signal from said interface, and
   a processor with programmed instructions for controlling:
      (a) variation of the pressure at the interface to provide ventilatory support to the patient;
      (b) a determination of a measure of a degree of dynamic airway compression as a function of data representing the airflow by measuring airway conductance separately during inspiratory and expiratory portions of at least one respiratory cycle; and
      (c) increasing or decreasing expiratory pressure in accordance with the derived measure of the degree of dynamic airway compression, wherein the measure of the degree of dynamic airway conductance is calculated as a function of the difference between the inspiratory conductance and the expiratory conductance.

20. The apparatus of claim 19 in which said instructions for increasing or decreasing the pressure during expiration perform said increase or decrease by servo-controlling the measure of the degree of dynamic airway compression.

21. The apparatus of claim 20 in which expiratory pressure is increased if said measure of the degree of dynamic airway compression is large or increasing, and expiratory pressure is reduced if said measure of the degree of dynamic airway compression is small or zero.

22. The apparatus of claim 21 in which expiratory pressure is increased if said measure of the degree of dynamic airway compression is large or increasing, and expiratory pressure is reduced if said measure of the degree of dynamic airway compression is small or zero.

23. The apparatus of claim 19 in which said measure of the degree of dynamic airway compression is based upon a respiratory airflow determination made across a plurality of respiratory cycles.

24. The apparatus of claim 19 in which the separate conductances during inspiration and expiration are measured in accordance with instructions controlling the substeps of:

superimposing a high-frequency oscillation on the variable pressure provided to the patient's airway, identifying the inspiratory and expiratory portions of each respiratory cycle, measuring the component of the respiratory airflow at said high frequency, separately over the inspiratory and expiratory portions of at least one respiratory cycle, and calculating the inspiratory and expiratory airway conductances from the high-frequency component airflow measurements.

* * * * *